(12) United States Patent
Ishihara et al.

(10) Patent No.: US 8,735,582 B2
(45) Date of Patent: May 27, 2014

(54) METHOD FOR PRODUCING CARBOXYLIC ANHYDRIDE AND ARYLBORONIC ACID COMPOUND

(75) Inventors: Kazuaki Ishihara, Nagoya (JP); Akira Sakakura, Nagoya (JP)

(73) Assignee: National University Corporation Nagoya University, Aichi (JP)

( * ) Notice: Subject to any disclaimer, the term of this patent is extended or adjusted under 35 U.S.C. 154(b) by 302 days.

(21) Appl. No.: 13/255,426

(22) PCT Filed: Mar. 3, 2010

(86) PCT No.: PCT/JP2010/053442
§ 371 (c)(1), (2), (4) Date: Sep. 8, 2011

(87) PCT Pub. No.: WO2010/103976
PCT Pub. Date: Sep. 16, 2010

(65) Prior Publication Data
US 2011/0319620 A1   Dec. 29, 2011

(30) Foreign Application Priority Data

Mar. 11, 2009 (JP) ................................. 2009-058720

(51) Int. Cl.
*C07F 5/02* (2006.01)
*C07F 5/00* (2006.01)

(52) U.S. Cl.
USPC ............................................... 546/13; 562/7

(58) Field of Classification Search
USPC .......................... 546/13; 568/6; 564/8; 562/7
See application file for complete search history.

(56) References Cited

U.S. PATENT DOCUMENTS

2005/0020839 A1   1/2005 Masuda et al.

FOREIGN PATENT DOCUMENTS

| JP | A-03-176484 | 7/1991 |
|---|---|---|
| JP | A-2001-335571 | 12/2001 |
| JP | A-2005-029572 | 2/2005 |
| JP | A-2006-045150 | 2/2006 |
| WO | WO 2004/113351 A2 | 12/2004 |
| WO | WO 2009/030022 A1 | 3/2009 |

OTHER PUBLICATIONS

Johnson, L. et al.: A drug targeting motif for glycosidase inhibitors: an iminosugar-boronate shows unexpectedly selective beta-galactosidase inhibition. Tetrahed. Letters, vol. 43, pp. 8905-8908, 2002.*
Lauer, M. et al.: Uber eine auberordentliche erhohung der reaktivitat von arylboronsauren durch nachbargruppen. Chem. Ber., vol. 118, pp. 246-260, 1985.*
Hawkins, R. et al.: Arylboronic acids. Aminoboronic anhydrides and a new heterocycle containing boron. J. of the american chemical Soc., vol. 82, pp. 3863-3866, 1960.*
Lauer et al., "Aryiboronic Acids with Intramolecular B—N Interaction: Convenient Synthesis Through *ortho*-Lithiation of Substituted Benzylamines," *Journal of Organometallic Chemistry*, vol. 256, pp. 1-9, 1983.
Arnold at al., "To Catalyze or not to Catalyze? Insight into Direct Amide Bond Formation from Amines and Carboxylic Acids under Thermal and Catalyzed Conditions," *Advanced Synthesis and Catalysts*, vol. 348, pp. 813-820, 2006.
Maki et al., "New boron(III)-catalyzed amide and ester condensation reactions," *Tetrahedron*, vol. 63, pp. 8645-8657, 2007.
Dong at al., "Two-Dimensional Scaffolds for the Parallel Alignment of Rod-Shaped Conjugated Molecules," *Journal of Organic Chemistry*, vol. 72, pp. 617-625, 2007.
Coghlan et al., "Synthesis and structure of potential Lewis acid-Lewis base bifunctional catalysts: 2-*N,N*-Diisopropylaminophenylboronate derivatives," *Journal of Organometallic Chemistry*, vol. 690, pp. 4784-4793, 2005.
Takeuchi et al., "Efficient Glucoside Extraction Mediated by a Boronic Acid with an Intramolecular Quaternary Ammonium Ion," *Tetrahedron*, vol. 52, No. 40, pp. 12931-12940, 1996.
International Search Report issued in Application No. PCT/JP2010/053442; Dated Apr. 6, 2010 (With Translation).
International Preliminary Report on Patentability issued in Application No. PCT/JP2010/053442; Dated Oct. 18, 2011.

* cited by examiner

*Primary Examiner* — Charanjit Aulakh
(74) *Attorney, Agent, or Firm* — Oliff PLC

(57) ABSTRACT

When phthalic acid is heated in heptane under azeotropic reflux conditions in the presence of a catalytic amount of an arylboronic acid compound (such as 2,6-(diisopropylaminomethyl)phenylboronic acid or 2,6-bis(diisopropylaminomethyl)phenylboronic acid), phthalic anhydride is obtained in high yield.

4 Claims, No Drawings

METHOD FOR PRODUCING CARBOXYLIC ANHYDRIDE AND ARYLBORONIC ACID COMPOUND

TECHNICAL FIELD

The present invention relates to a method for producing a carboxylic anhydride and an arylboronic acid compound usable as a catalyst therefor.

BACKGROUND ART

As a method for producing a carboxylic anhydride, there have been known a reaction between a carboxylic acid and a carboxylic acid chloride and direct heating of a carboxylic acid. In the former case, since a large amount of hydrochloric acid is generated, a base in an amount in moles at least equivalent thereto must be used for neutralization, and hence the cost and time are increased. On the other hand, in the latter case, severe reaction conditions (300° C. or more) are required, and the yield is low. Besides those classical production methods, in Patent Document 1, a method for producing a phthalic anhydride derivative has been reported in which a dehydration reaction of a phthalic acid derivative is performed in an inert solvent in the presence of a catalytic amount of an acidic compound. As the acidic compound, for example, para-toluenesulfonic acid (p-TsOH), trifluoromethanesulfonic acid, polyphosphoric acid, and sulfuric acid are usable. For example, when phthalic acid was heated in toluene in the presence of a catalytic amount of p-TsOH under azeotropic reflux conditions with the removal of water, phthalic anhydride was obtained with a yield of 95%.

Patent Document 1: JP 2001-335571 A

DISCLOSURE OF INVENTION

However, since the acidic compounds, such as p-TsOH, are strong acids, there has been a problem in that when an iron-based (such as stainless steel (SUS)) reaction vessel is used, corrosion is liable to occur. In addition, there has also been a problem in that when a chain anhydride is produced in the presence of the strong acid as mentioned above, since a reverse reaction, that is, a hydrolysis reaction of an anhydride, is liable to occur if a small amount of water is present, the reaction is difficult to control.

The present invention was made in order to solve the problems described above, and an object of the present invention is to produce under mild acidic conditions, an aromatic carboxylic anhydride and a chain aliphatic carboxylic anhydride having saturated bond between α and β carbons as well as a cyclic carboxylic anhydride.

In order to achieve the above object, the present inventors found that when phthalic acid was heated in heptane in the presence of a catalyst amount of an arylboronic acid compound (such as 2-(diisopropylaminomethyl)phenylboronic acid or 2,6bis (diisopropylaminomethyl)phenylboronic acid) under azeotropic reflux conditions with the removal of water, phthalic anhydride can be obtained with a high yield, and the present invention was finally made.

That is, a method for producing a carboxylic anhydride according to the present invention is a method for producing a cyclic carboxylic anhydride by intramolecular dehydrative condensation of a dicarboxylic acid compound and producing an aromatic carboxylic anhydride or a chain aliphatic carboxylic anhydride having saturated bond between α and β carbons by intermolecular dehydrative condensation of two carboxylic acid compounds. As a catalyst, there is used an arylboronic acid compound which has at least one heteroatom-containing substituent on at least one ortho position with one carbon atom provided therebetween, the heteroatom-containing substituent containing a nitrogen atom or a phosphorous atom which has no hydrogen atom.

A method for producing an imide compound according to the present invention is a method for producing a cyclic imide compound in which a dicarboxylic acid compound and a primary amine compound are allowed to react with each other to form a cyclic imide compound, and as a catalyst, there is used an arylboronic acid compound which has at least one heteroatom-containing substituent on at least one ortho position with one carbon atom provided therebetween, the heteroatom-containing substituent containing a nitrogen atom or a phosphorous atom which has no hydrogen atom.

The arylboronic acid compound according to the present invention is a compound having —$CH_2NR^1R^2$ ($R^1$ and $R^2$ each independently represent an alkyl group, an alkyl group having a cycloalkyl group, an alkyl group having a halogen atom, a cycloalkyl group, a cycloalkyl group having an alkyl group, or a cycloalkyl group having a halogen atom, or $R^1$ and $R^2$ are bonded to each other to form a nitrogen-containing hetero ring in the form of $NR^1R^2$) on each of the two ortho positions or a compound having at least one nitrogen-containing five- or six-membered aromatic ring group on at least one ortho position.

According to the method for producing a carboxylic anhydride of the present invention, besides a cyclic carboxylic anhydride, an aromatic carboxylic anhydride and a chain aliphatic carboxylic anhydride having saturated bond between α and β carbons can be produced under mild acidic conditions. In addition, according to the method for producing an imide compound of the present invention, a cyclic imide compound can be produced by one step under mild acidic conditions. In addition, the arylboronic acid compound according to the present invention is suitable as a catalyst for producing a cyclic carboxylic anhydride by intramolecular dehydrative condensation of a dicarboxylic acid compound and producing an aromatic carboxylic anhydride or a chain aliphatic carboxylic anhydride having saturated bond between α and β carbons by intermolecular dehydrative condensation of two carboxylic acid compounds.

A carboxylic anhydride can be produced under mild acidic conditions according to the present invention, and the reason for this is believed as described below (see the following formula). In the following formula, 2-(dialkylaminomethyl)phenylboronic acid and alkane acid will be described as an arylboronic acid compound and a carboxylic acid, respectively, by way of example. First, the carboxylic acid and the arylboronic acid compound form a mixed acid anhydride of carboxylic acid-arylboronic acid, so that the carboxylic acid is activated thereby (Step 1). Another molecule of the carboxylic acid is activated by forming a salt with an amino group of the arylboronic acid compound of this mixed acid anhydride and is allowed to react with the carboxylic acid thereof, so that a carboxylic anhydride is generated (Step 2). In addition, when a cyclic imide compound is produced by one step, it is estimated that after the carboxylic anhydride is produced in Step 2, the carboxylic anhydride and a primary amine in the system are allowed to react with each other to produce an imide compound.

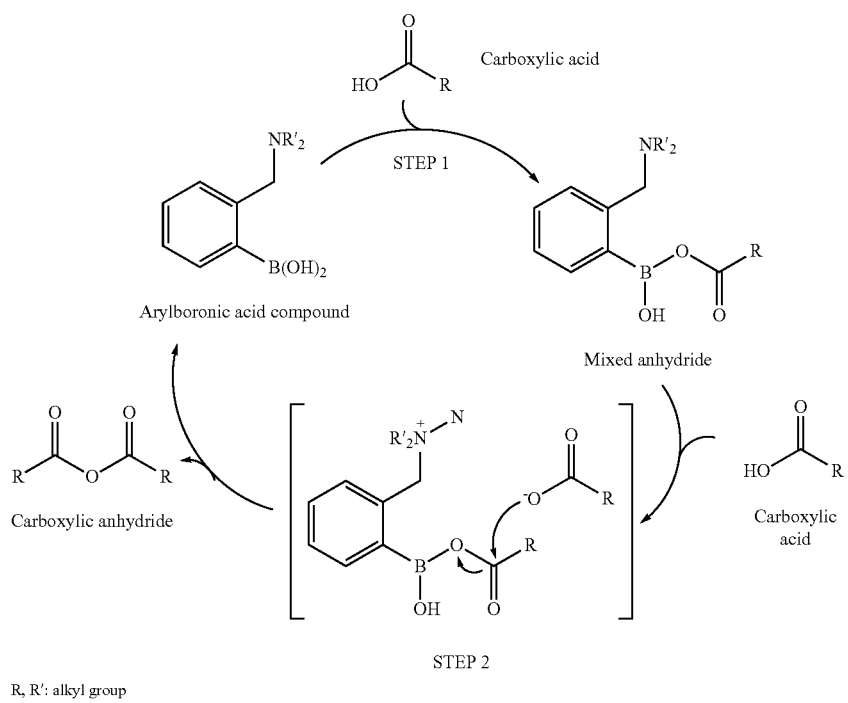

R, R': alkyl group

BEST MODES FOR CARRYING OUT THE INVENTION

A method for producing a carboxylic anhydride according to the present invention is a method for producing a cyclic carboxylic anhydride by intramolecular dehydrative condensation of a dicarboxylic acid compound and producing an aromatic carboxylic anhydride or a chain aliphatic carboxylic anhydride having saturated bond between α and β carbons by intermolecular dehydrative condensation of two carboxylic acid compounds. An arylboronic acid compound is used as a catalyst, the arylboronic acid compound having at least one heteroatom-containing substituent on at least one ortho position with one carbon atom provided therebetween, the heteroatom-containing substituent containing a nitrogen atom or a phosphorous atom which has no hydrogen atom. In this embodiment, the dicarboxylic acid compound which performs intramolecular dehydrative condensation is a compound having at least one dicarboxylic acid structure in which carboxylic acid groups are bonded to respective two carbons, and for example, a dicarboxylic acid compound and a tetracarboxylic acid compound may be mentioned. In particular, as the dicarboxylic acid compound, for example, phthalic acid, cyclohexane-1,2-dicarboxylic acid, and cyclopentane-1,2-dicarboxylic acid may be mentioned, and as the tetracarboxylic acid compound, for example, benzene-1,2,4,5-tetracarboxylic acid (pyromellitic acid) and diphenyl ether-3,3',4,4'-tetracarboxylic acid may be mentioned. In addition, as the aromatic carboxylic acid compound which performs intermolecular dehydration condensation, for example, benzoic acid may be mentioned, and as the chain aliphatic carboxylic anhydride having saturated bond between α and β carbons, for example, butanoic acid, pentanoic acid, and hexanoic acid may be mentioned. The aromatic carboxylic acid compound and the aliphatic carboxylic acid compound mentioned above each may have at least one substituent, such as an aryl group, a cycloalkyl group, a nitro group, a cyano group, or halogen.

As the carboxylic acid compound described above, a compound having a boiling point of 160° C. or more is preferable in order to efficiently advance the reaction.

A method for producing an imide compound according to the present invention is a method for producing a cyclic imide compound by allowing a dicarboxylic acid compound and a primary amine compound to react with each other, and an arylboronic acid compound is used as a catalyst, the arylboronic acid compound having at least one heteroatom-containing substituent on at least one ortho position with one carbon atom provided therebetween, the heteroatom-containing substituent containing a nitrogen atom or a phosphorous atom which has no hydrogen atom. In this embodiment, the dicarboxylic acid compound is a compound having at least one dicarboxylic acid structure in which carboxylic acid groups are bonded to respective two carbons, and for example, a dicarboxylic acid compound and a tetracarboxylic acid compound may be mentioned. In particular, as the dicarboxylic acid compound, for example, phthalic acid, cyclohexane-1,2-dicarboxylic acid, and cyclopentane-1,2-dicarboxylic acid may be mentioned, and as the tetracarboxylic acid compound, for example, benzene-1,2,4,5-tetracarboxylic acid (pyromellitic acid) and diphenyl ether-3,3',4,4'-tetracarboxylic acid may be mentioned. In addition, as the primary amine compound, for example, an arylamine, an alkylamine, and a cycloalkylamine may be mentioned. As the arylamine, for example aniline, toluidine, dimethylaniline, cumenylamine, mesitylamine, and pyridinylamine may be mentioned. As the alkylamine, for example, an amine having an alkyl group of 1 to 10 carbon atoms, such as n-hexylamine and n-octylamine, may be mentioned. As the cycloalkylamine, for example, cyclopentylamine and cyclohexylamine may be mentioned.

In the method for producing a carboxylic anhydride and the method for producing an imide compound, according to the present invention, as the heteroatom-containing substituent of the arylboronic acid compound, —CH$_2$NR$^1$R$^2$ (R$^1$ and R$^2$ each independently represent an alkyl group, an alkyl group having a cycloalkyl group, an alkyl group having a halogen atom, a cycloalkyl group, a cycloalkyl group having an alkyl group, or a cycloalkyl group having a halogen atom, or R$^1$ and R$^2$ are bonded to each other to form a nitrogen-containing hetero ring in the form of NR$^1$R$^2$) is preferable. In this case, as the alkyl group, for example, a methyl group, an ethyl group, a propyl group, an isopropyl group, an n-butyl group, an isobutyl group, a sec-butyl group, a tert-butyl group, a 2-methyl-1-butyl group, an n-amyl group, a sec-amyl group, an isoamyl group, a tert-amyl group, a neopentyl group, and 3-pentyl group may be mentioned. As the cycloalkyl group, although a cyclopropyl group, a cyclopentyl group, a cyclohexyl group, a cycloheptyl group, and the like may be mentioned, among those mentioned above, an alkyl group having a branch is preferable, and an isopropyl group is more preferable. As the halogen atom, for example, a fluorine atom, a chlorine atom, a bromine atom, and an iodine atom may be mentioned. When the nitrogen-containing hetero ring is formed by bonding in the form of NR$^1$R$^2$, as the nitrogen-containing hetero ring, for example, a nitrogen-containing aromatic compound, such as pyridine, N-alkyl imidazole, pyrimidine, pyridazine, or pyrazine, or a nitrogen-containing alicyclic compound, such as piperidine, may be mentioned. Among those mentioned above, a nitrogen-containing aromatic compound is preferable, and pyridine is more preferable. These nitrogen-containing hetero rings each may have at least one substituent, such as an alkyl group, a cycloalkyl group, an aryl group, a nitro group, a cyano group, or a halogen atom, on the ring.

In the method for producing a carboxylic anhydride and the method for producing an imide compound, according to the present invention, as the heteroatom-containing substituent of the arylboronic acid compound, a group represented by the following formula (1) is preferable (R$^6$ to R$^9$ each independently represent an alkyl group or an alkyl group having a halogen atom), and R$^6$ to R$^9$ each preferably represent the same alkyl group. In this case, even if the catalyst amount is small (such as 1 percent by mole), a carboxylic anhydride can be obtained in high yield. As the alkyl group, for example, a methyl group, an ethyl group, a propyl group, an isopropyl group, an n-butyl group, an isobutyl group, a sec-butyl group, a tert-butyl group, 2-methyl-1-butyl group, an n-amyl group, a sec-amyl group, an isoamyl group, a tert-amyl group, a neopentyl group, and 3-pentyl group may be mentioned; however, among those mentioned above, a methyl group is particularly preferable. As the halogen atom, for example, a fluorine atom, a chlorine atom, a bromine atom, and an iodine atom may be mentioned.

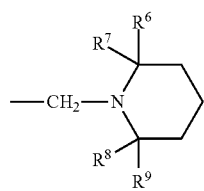

(1)

In the method for producing a carboxylic anhydride and the method for producing an imide compound, according to the present invention, as the heteroatom-containing substituent of the arylboronic acid compound, —CH$_2$Z$^+$R$^3$R$^4$R$^5$X$^-$ is preferable (Z represents a nitrogen atom or a phosphorus atom; R$^3$ to R$^5$ each independently represent an alkyl group, an alkyl group having a cycloalkyl group, an alkyl group having a halogen atom, a cycloalkyl group, a cycloalkyl group having an alkyl group, or a cycloalkyl group having a halogen atom; and X represents an anionic group). In this case, for the alkyl group, the cycloalkyl group, and the halogen atom, since those previously mentioned above by way of example are usable, description thereof is omitted. Although the anionic group is not particularly limited, for example, a fluorine ion, a chlorine ion, a bromine ion, and an iodine ion may be mentioned.

In the method for producing a carboxylic anhydride and the method for producing an imide compound, according to the present invention, although the arylboronic acid compound may have the heteroatom-containing substituent mentioned above only one ortho position, the heteroatom-containing substituents are preferably located on the two ortho positions. When being located on the two ortho positions, the heteroatom-containing substituents may be identical to or different from each other.

In the method for producing a carboxylic anhydride and the method for producing an imide compound, according to the present invention, the arylboronic acid compound may have at least one substituent (such as a halogen atom, an alkyl group, a nitro group, or an alkyl group having a halogen atom) on its benzene ring. The substituent as described above is preferably located on the para position of the benzene ring. For the halogen atom and the alkyl group, since those previously mentioned above by way of example are usable, description thereof is omitted.

In the method for producing a carboxylic anhydride and the method for producing an imide compound, according to the present invention, the amount of the arylboronic acid compound is preferably 0.5 to 50 percent by mole to 1 mol of the carboxyl group and more preferably 1 to 10 percent by mole.

In the method for producing a carboxylic anhydride and the method for producing an imide compound, according to the present invention, although a reaction solvent is not particularly limited as long as it has no adverse influences on intramolecular dehydrative condensation and intermolecular dehydrative condensation, for example, a hydrocarbon solvent, a nitrile solvent, a nitro solvent, an ether solvent, and an amide solvent are preferable, and a nitrile solvent is particularly preferable. As the hydrocarbon solvent, for example, hexane, heptane, octane, nonane, toluene, and xylene may be mentioned. As the nitrile solvent, for example, butyronitrile and propionitrile may be mentioned. As the nitro solvent, for example, nitromethane and nitroethane may be mentioned. As the ether solvent, for example, anisole and dioxane may be mentioned. As the amide solvent, for example, N,N-dimethylformamide (DMF) and N-methyl pyrrolidone (NMP) may be mentioned. In addition, a mixed solvent formed therefrom may also be used.

In the method for producing a carboxylic anhydride and the method for producing an imide compound, according to the present invention, although a reaction temperature may be appropriately set in consideration of a reaction rate, the ratio of by-products, and the like, for example, the temperature is preferably set in a range of 20° C. to 200° C. and more preferably in a range of 60° C. to 160° C. In addition, in the intramolecular dehydrative condensation and the intermolecular dehydrative condensation, although water is generated together with a carboxylic anhydride, it is preferable that the water be efficiently removed in order to improve the yield of the carboxylic anhydride. For example, the reaction temperature is set to a reflux temperature (that is, boiling point) of the solvent, and azeotropic reflux with the removal of water is preferably performed. The point described above may also be applied to the method for producing an imide compound. In the method for producing a carboxylic anhydride and the method for producing an imide compound, according to the present invention, although a reaction time may be appropriately set in accordance with a reactive substrate, a reaction temperature, and the like, the time is generally several minutes to several tens of hours. In addition, the intramolecular dehydrative condensation and the intermolecular dehydrative condensation may be performed until the reactive substrate is thoroughly consumed; however, when the consumption rate of the reactive substrate is extremely decreased as the reaction progresses, it is preferable in some cases that even if the reactive substance is not thoroughly consumed, the carboxylic anhydride be recovered by finishing the reaction. The point described above may also be applied to the method for producing an imide compound.

In the method for producing a carboxylic anhydride and the method for producing an imide compound, according to the present invention, in order to isolate target carboxylic anhydride and imide compound, a commonly known isolation method may be used. For example, after the reaction solvent in a reaction mixture is evaporated under reduced pressure, purification is performed by column chromatography, recrystallization, or the like, so that the target carboxylic anhydride and imide compound can be isolated.

The arylboronic acid compound according to the present invention is a compound having —$CH_2NR^1R^2$ ($R^1$ and $R^2$ each independently represent an alkyl group, an alkyl group having a cycloalkyl group, an alkyl group having a halogen atom, a cycloalkyl group, a cycloalkyl group having an alkyl group, or a cycloalkyl group having a halogen atom, or $R^1$ and $R^2$ are bonded to each other to form a nitrogen-containing hetero ring in the form of $NR^1R^2$) on each of the two ortho positions or a compound having a nitrogen-containing five- or six-membered aromatic ring group on at least one ortho position. Although —$CH_2NR^1R^2$ is the same as described above, a diisopropylaminomethyl group and a trioctylammonium methyl group are preferable. As the nitrogen-containing five- or six-membered aromatic ring group, although a pyridyl group, a pyrimidyl group, a pyridazyl group, a pyrazyl group, an N-alkyl imidazole group may be mentioned by way of example, a pyridyl group, in particular, 2-pyridyl group, or an N-alkyl imidazole group is preferable. Those arylboronic acid compounds each may have a halogen atom, an alkyl group, or an alkyl group having a halogen atom on its benzene ring. For the halogen atom and the alkyl group, since those previously mentioned above by way of example are usable, description thereof is omitted. In addition, as the above —$CH_2NR^1R^2$, a group represented by the above formula (1) ($R^6$ to $R^9$ are the same as described above by way of example) is preferable.

EXAMPLES

Example 1

Phthalic acid (2.5 mmol), 2,6-bis(diisopropylaminomethyl)phenylboronic acid (hereinafter, referred to as "boronic acid compound A", 0.25 mol) as an arylboronic acid catalyst, and heptane (10 mL) as a solvent were added in a flask having a volume of 20 mL, and a column (small Soxhlet extractor) filled with dried molecular sieves 3A (approximately 3 g) was fitted to the flask. The mixture was heated for 12 hours under azeotropic reflux conditions with the removal of water. After the reaction mixture was cooled to room temperature, heptane was evaporated under reduced pressure. The crude product of phthalic anhydride thus obtained was analyzed by $^1$H NMR (CDCl$_3$), and the yield thereof was calculated. When the same procedure was repeatedly performed a plurality of times, the yield was 72% to 81%.

In addition, the chemical shift (ppm) of $^1$H NMR was as follows; phthalic acid: δ 7.51-7.60 (m, 2H), and phthalic anhydride: δ 8.05-8.14(m, 2H).

Examples 2 to 9, Comparative Examples 1 to 4

In Examples 2 to 9 and Comparative Examples 1 to 4, in accordance with Example 1, phthalic anhydride was produced under the conditions shown in Table 1. The results are shown in Table 1. In addition, the result of Example 1 is also collectively shown in Table 1. As apparent from Table 1, in the case of no catalyst, phthalic anhydride was not obtained when heptane having a low boiling point was used as a solvent (Comparative Example 1), and when nonane having a high boiling point was used as a solvent, although phthalic anhydride was obtained, the yield was as low as 12% (Comparative Example 2). In addition, when p-TsOH, the catalyst disclosed in Patent Document 1, was used, although phthalic anhydride was obtained with a high yield of 88% (Comparative Example 3), since this catalyst was a strong acid, for example, corrosion of an iron-based reaction vessel was concerned. Furthermore, when 2,4,6-trimethylphenylboronic acid (having no dialkylaminomethyl group on the ortho position) was used as the catalyst, phthalic anhydride was obtained only in low yield of 7% (Comparative Example 4). On the other hand, when the boronic acid compound A or a derivative thereof having a t-butyl group or a fluorine atom on the para position thereof (referred to as "boronic acid compound B" and "boronic acid compound C", respectively) was used as the catalyst as in Examples 1 to 6, although the acids mentioned above were each milder than p-TsOH, phthalic anhydride was obtained in good yield (particularly Examples 4 and 5). In addition, when 2-(diisopropylaminomethyl)phenylboronic acid (see J Organometallic Chem., 2005, vol. 690, pp. 4,784 to 4,793) having a dialkylaminomethyl group on one ortho position was used as the catalyst as in Example 7, when a phenylboronic acid having 2-pyridyl group on one ortho position (hereinafter referred to as "boronic acid compound D") was used as the catalyst as in Example 8, or also when a phenylboronic acid having an ammonium salt which included no hydrogen atoms on one ortho position with one carbon atom provided therebetween (see Tetrahedron, 1999, vol. 55, pp. 2,857 to 2,864, Tetrahedron, 1996, vol. 52, and pp. 12,931 to 12,940.) was used as the catalyst as in Example 9, phthalic anhydride was obtained in high yield. In addition, also when the 2-pyridyl group on the ortho position in Example 8 was replaced with a 3-pyridyl group or an N-methyl-2-imidazolyl group, in the synthesis reaction of phthalic anhydride (however, octane was used as the solvent), activity almost equivalent to that obtained in the case of the 2-pyridyl group was obtained.

TABLE 1

Reaction scheme: Phthalic acid (benzene-1,2-dicarboxylic acid) → phthalic anhydride, with Catalyst (10 mol %), Solvent, Dehydration by heating and refluxing.

| | Catalyst | Solvent (Boiling point) | Substrate concentration | Reaction time | Yield | |
|---|---|---|---|---|---|---|
| EXAMPLE 1 | Boronic acid compound A/B/C (2,6-bis(diisopropylaminomethyl)phenylboronic acid, R = H/t-Bu/F) | Heptane (98° C.) | 0.25M | 12 h | R = H | 72-81% |
| EXAMPLE 2 | | | | | R = t-Bu | 52% |
| EXAMPLE 3 | | | | | R = F | 48% |
| EXAMPLE 4 | | Octane (125-127° C.) | 0.5M | 0.5 h | R = H | 100% |
| EXAMPLE 5 | | Butyronitrile (115-117° C.) | 0.5M | 2.5 h | | 92% |
| EXAMPLE 6 | | Nitroethane (114° C.) | 0.5M | 2.5 h | | 65% |

R = H: Boronic acid compound A
R = t-Bu: Boronic acid compound B
R = F: Boronic acid compound C

| | Catalyst | Solvent (Boiling point) | Substrate concentration | Reaction time | Yield |
|---|---|---|---|---|---|
| EXAMPLE 7 | 2-(diisopropylaminomethyl)phenylboronic acid | Nonane (151° C.) | 0.5M | 0.5 h | 83% |
| EXAMPLE 8 | 2-(pyridin-2-yl)phenylboronic acid | Nonane (151° C.) | 0.5M | 5.5 h | 100% |
| EXAMPLE 9 | Boronic acid compound D (trioctyl(2-boronobenzyl)ammonium bromide) | Heptane (98° C.) | 0.5M | 29 h | 71% |
| COMPARATIVE EXAMPLE 1 | No catalyst | Heptane (98° C.) | 0.2 M | 12 h | 0% |
| COMPARATIVE EXAMPLE 2 | No catalyst | Nonane (151° C.) | 0.5M | 5.5 h | 12% |
| COMPARATIVE EXAMPLE 3 | p-TsOH | Heptane (98° C.) | 0.25M | 12 h | 88% |
| COMPARATIVE EXAMPLE 4 | 2,4,6-trimethylphenylboronic acid | Heptane (98° C.) | 0.25M | 12 h | 7% |

Examples 10 to 13, Comparative Example 5 to 8

In Examples 10 to 13 and Comparative Example 5 to 8, in accordance with Example 1, a carboxylic anhydride was produced from a dicarboxylic acid under conditions shown in Table 2. The yield was calculated by analyzing a crude product using $^1$H NMR (CDCl$_3$). Incidentally, the chemical shift (ppm) of $^1$H NMR was as follows; trans-cyclopentane-1,2-dicarboxylic acid: δ 2.9-3.15 (m, 2H), an anhydride thereof (cis-carboxylic anhydride): δ 3.5-3.7 (m, 2H), cis-cyclohexane-1,2-dicarboxylic-acid: δ 2.66 (m, 2H), an anhydride thereof: δ 3.33 (m, 2H), trans-cyclohexane-1,2-dicarboxylic acid: δ 2.66 (m, 2H), an anhydride thereof (cis-carboxylic anhydride): δ 3.33 (m, 2H), pyromellitic acid: δ 7.90 (s, 2H), a monoanhydride thereof: δ 8.25 (s, 2H), and a dianhydride thereof: δ 8.72 (s, 2H).

In Examples 10 to 13, the boronic acid compound A was used as the catalyst, and in Comparative Examples 5 to 8, p-TsOH was used as the catalyst. The results are shown in Table 2. As apparent from Table 2, when cis-cyclohexane-1,2-dicarboxylic acid was used as the substrate, regardless of whether the boronic acid compound A or p-TsOH was used as the catalyst, a corresponding cis-carboxylic anhydride was obtained in significantly high yield (in Example 10 and Comparative Example 5). On the other hand, in the case in which trans-cyclopentane-1,2-dicarboxylic acid was used as the substrate, when the catalyst is the boronic acid compound A, after the trans configuration was epimerized to the cis configuration, a corresponding cis-carboxylic anhydride was obtained almost quantitatively by the intramolecular dehydrative condensation (Example 11); however, when the catalyst was p-TsOH, the cis-carboxylic anhydride mentioned above was obtained only in 16% yield (Comparative Example 6). In addition, in the case in which trans-cyclohexane-1,2-dicarboxylic acid was used as the substrate, in a manner similar to that described above, when the catalyst was boronic acid compound A, after the trans configuration was epimerized to the cis configuration, a corresponding cis-carboxylic anhydride was obtained in high yield of 95% by the intramolecular dehydrative condensation (Example 12); however, when the catalyst was p-TsOH, the cis-carboxylic anhydrides mentioned above was hardly obtained (Comparative Example 7). It was found that from the results described above, when trans-1,2-dicarboxylic acid compound was used as the substrate, the boronic acid compound A was particularly effective. Furthermore, in the case in which benzene-1,2,4,5-tetracarboxylic acid (pyromellitic acid) was used as the substrate, when the catalyst was the boronic acid compound A, pyromellitic dianhydride to be used as a raw material of a heat-resistant polyimide was quantitatively obtained (Example 13); however, when the catalyst was p-TsOH, pyromellitic dianhydride was obtained only in low yield (Comparative Example 8).

TABLE 2

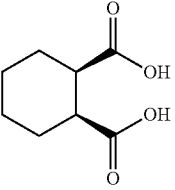 [SMILES: O=C(O)[C@H]1CCCC[C@H]1C(=O)O]

| | Catalyst | Dicarboxylic acid | Carboxylic acid anhydride | Yield |
|---|---|---|---|---|
| EXAMPLE 10 | Boronic acid compound A | 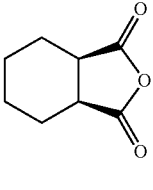 | 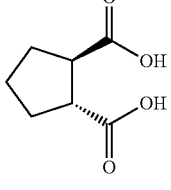 | 95% |
| COMPARATIVE EXAMPLE 5 | p-TsOH | | | 99% |
| EXAMPLE 11 | Boronic acid compound A | 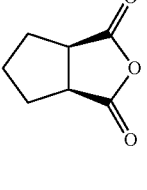 | 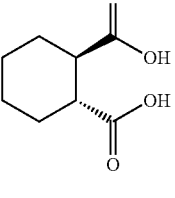 | >96% |
| COMPARATIVE EXAMPLE 6 | p-TsOH | | | 16% |
| EXAMPLE 12 | Boronic acid compound A | 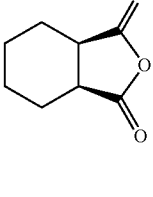 | | 95% |
| COMPARATIVE EXAMPLE 7 | p-TsOH | | | 1% |

TABLE 2-continued

| | Catalyst | Dicarboxylic acid | Carboxylic acid anhydride | Yield |
|---|---|---|---|---|
| EXAMPLE 13 [×1] | Boronic acid compound A | (benzene-1,2,4,5-tetracarboxylic acid) | (pyromellitic dianhydride) | >99% [×2] (<1%) |
| COMPARATIVE EXAMPLE 8 [×1] | p-TsOH | | | 22% [×2] (20%) |

[×1] Butironitrile was used in stead pf octane, and reaction was performed for 24 hours.
[×2] Value in parenthesis is yield of monoanhydride.

Examples 14 to 16, Comparative Examples 9 and 10

In Examples 14 to 16 and Comparative Examples 9 and 10, in accordance with Example 1, a carboxylic anhydride was produced under conditions shown in Table 3 by the intermolecular dehydrative condensation of 4-phenylbutanoic acid (4-phenylbutyric acid). As apparent from Table 3, although the carboxylic anhydride was not obtained without using catalyst (Comparative Example 9), when p-TsOH was used as the catalyst, the carboxylic anhydride was obtained with a yield of 18% (Comparative Example 10). On the other hand, when the boronic acid compound A, phenylboronic acid having a diisopropylaminomethyl group on the ortho position (which was described above), or phenylboronic acid having a (2,2,6,6-tetramethylpiperazinyl)methyl group on the ortho position (see WO 2004/113351) was used as the catalyst, although each of those acids was milder than p-TsOH, the carboxylic anhydride was obtained in 18% to 22% yield, which was equivalent to that obtained by p-TsOH (Examples 14 to 16).

TABLE 3

Ph-(CH2)3-COOH →[Catalyst (10 mol %), Nonane (0.25M), Dehydration by heating and refluxing (bp 151° C.) 12 h] Ph-(CH2)3-C(O)-O-C(O)-(CH2)3-Ph

| Catalyst | | Yield |
|---|---|---|
| EXAMPLE 14 | Boronic acid compound A | 22% |

TABLE 3-continued

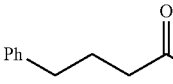

| | Catalyst | Yield |
|---|---|---|
| EXAMPLE 15 | 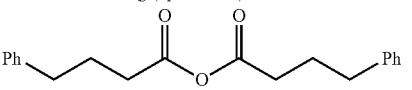 | 18% |
| EXAMPLE 16 | 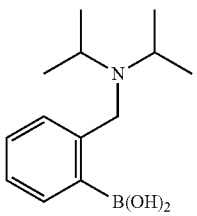 [SMILES: CC(C)N(Cc1ccccc1B(O)O)C(C)C] | 18% |
| COMPARATIVE EXAMPLE 9 | No catalyst | 0% |
| COMPARATIVE EXAMPLE 10 | p-TsOH | 18% |

Example 17

The boronic acid compound A was synthesized as described below. That is, 2-bromo-1,3-dimethylbenzene (Polyhedron, 2002, vol. 21, pp. 2,827 to 2,834.) (60 mmol), carbon tetrachloride (350 mL), N-bromosuccinimide (126 mmol), and benzoyl peroxide (purity: 75%, 1.8 mmol) were sequentially added in a flask having a volume of 1 L. The mixture was refluxed for 24 hours. After a reaction mixture was concentrated under reduced pressure. The residue was suspended in chloroform, and an insoluble matter was separated by filtration. After the filtrate was washed with water twice, the combined aqueous layer was extracted with chloroform. After these chloroform layers were mixed together, the organic solution was dried over anhydrous sodium sulfate, concentrated under reduced pressure. The crude product thus obtained was purified by a column chromatography (silica gel, hexane) and recrystallization (hexane), so that 2-bromo-1,3-bis(bromomethyl)benzene was obtained (11.0 g, yield: 53%). In a flask having a volume of 300 mL, 2-bromo-1,3-bis(bromomethyl)benzene (15 mmol) and diisopropylamine (600 mmol) were added. The mixture was refluxed for 43 hours. After an insoluble matter in the reaction mixture was removed by filtration, the filtrate was concentrated under reduced pressure. The residue was dissolved in chloroform and was then washed with water twice. The combined aqueous layer was extracted with chloroform. After these chloroform layers were mixed together, the organic solution was dried over anhydrous sodium sulfate, concentrated under reduced pressure. The crude product thus obtained was purified by column chromatography (NH silica gel, hexane), so that 2-bromo-1,3-bis(diisopropylaminomethyl)benzene was obtained (5.39 g, yield: 94%). In a flask having a volume of 50 mL filled with dry nitrogen, 2-bromo-1,3-bis(diisopropylaminomethyl)benzene (5.7 mmol), tetrahydrofuran (9.5 mL), and N,N,N',N'-tetramethylethylenediamine (11.4 mmol) were added and cooled to −78° C. After a 1.5-M hexane solution (7.3 mL, 11.4 mmol) of butyl lithium was added to this solution dropwise, the mixture was stirred at −78° C. for 1 hour. To the reaction mixture was added trimethyl borate (22.8 mmol), and the mixture was stirred at room temperature for 12 hours. After the reaction mixture was concentrated under reduced pressure, the residue was suspended in chloroform, and an insoluble matter was removed by filtration. After the filtrate was washed with water twice, the combined aqueous layer was extracted with chloroform. After these chloroform layers were mixed together, the organic solution was dried over anhydrous sodium sulfate, concentrated under reduced pressure. The crude product thus obtained was purified by column chromatography (NH silica gel, hexane-ethyl acetate: 5:1). After this product was dissolved in a mixture of water and methanol, the solvent was removed at 50° C. to 60° C. under reduced pressure, so that the boronic acid compound A was obtained (1.13 g, yield: 55%). The structure of the boronic acid compound A was identified by $^1$H NMR and $^{13}$C NMR. $^1$H NMR (CDCl$_3$) δ 1.09 (d, J=6.6 Hz, 24H), 3.04 (sept, J=6.6 Hz, 4H), 3.79 (s, 4H) 7.18-7.22 (m, 3H); $^{13}$C NMR (CDCl$_3$) δ 19.9, 46.9, 52.2, 128.4, 131.5, 142.8.

Example 18

The boronic acid compound B was synthesized from 2-bromo-5-t-butyl-1,3-dimethylbenzene (J. Org. Chem., 2003, vol. 68, p. 6,071 to 6,078.) by the same procedure as that for the boronic acid compound A (overall yield: 22%). The structure of the boronic acid compound B was identified by $^1$H NMR and $^{13}$C NMR. $^1$H NMR (CDCl$_3$) δ 1.09 (d, J=6.9 Hz, 24H), 1.32 (s, 9H), 3.03 (sept, J=6.9 Hz, 4H), 3.80 (s, 4H), 7.21 (s, 2H); $^{13}$C NMR (CDCl$_3$) δ 19.9, 31.0, 34.2, 46.8, 52.6, 128.5, 142.6, 151.1.

Example 19

The boronic acid compound C was synthesized from 2-bromo-5-fluoro-1,3-dimethylbenzene (Bull. Chem. Soc. Jpn., vol. 74, 2,207 to 2,218.) by the same procedure as that for the boronic acid compound A (overall yield: 11%). The structure of the boronic acid compound C was identified by $^1$H NMR and $^{13}$C NMR. $^1$H NMR (CDCl$_3$) δ 1.09 (d, J=6.9 Hz, 24H), 3.04 (sept, J=6.9 Hz, 4H), 3.77 (s, 4H), 6.93 (d, J=9.6 Hz, 2H); $^{13}$C NMR (CDCl$_3$) δ 19.9, 47.1, 52.1, 118.0 (d, J=19.1 Hz), 145.8 (d, J=6.7 Hz), 162.3 (d, J=246 Hz).

Example 20

The boronic acid compound D was synthesized as described below. That is, 2-(2-bromophenyl)pyridine (J. Am. Chem. Soc., 2006, vol. 128, p. 6,790 and 6,791.) (4.0 mmol) was added in a flask of 50 mL filled with dry nitrogen together with toluene (6.4 mL) and tetrahydrofuran (1.6 mL) as a solvent and was cooled to −78° C. After a 1.5-M hexane solution of butyl lithium (3.1 mL, 4.8 mmol) was added to this solution dropwise, and the mixture was stirred at −78° C. for 30 minutes. To the reaction mixture was added triisopropyl borate (4.8 mL), and the mixture was stirred at room temperature for 19 hours. After the reaction mixture was concentrated under reduced pressure, the residue was purified by column chromatography (alumina, ethyl acetate-methanol=5:1), so that methyl ester of the boronic acid compound D was obtained. After this product was dissolved in a mixture of water and methanol, the solvent was removed at 50° C. to 60° C. under reduced pressure, so that the boronic acid compound D was obtained (669 mg, yield: 84%). The structure of the boronic acid compound D was identified by $^1$H NMR and $^{13}$C NMR. $^1$H NMR (CD$_3$OD) δ 7.42 (dt, J=1.5, 7.5 Hz, 1H), 7.47 (dt, J=1.5, 7.5 Hz, 1H), 7.60 (ddd, J=0.9, 1.5, 7.5 Hz, 1H), 7.64 (ddd, J=1.5, 5.7, 7.5 Hz, 1H), 7.96 (ddd, J=1.2, 1.5, 7.5 Hz, 1H), 8.18 (ddd, J=1.2, 1.5, 8.1 Hz, 1H), 8.27 (ddd, J=1.5, 7.5, 8.1 Hz, 1H), 8.49 (ddd, J=0.9, 1.5, 5.7 Hz, 1H); $^{13}$C NMR (CD$_3$OD) δ 119.3, 123.2, 125.0, 129.5, 131.7, 132.3, 138.9, 143.1, 144.7, 157.1.

Examples 21 to 27

Phthalic acid (2.5 mmol), an arylboronic acid catalyst (0.025 mol, 1 percent by mole) shown in Table 4, and a solvent (10 mL) were added in a flask having a volume of 20 mL, and a column (small Soxhlet extractor) filled with dried molecular sieves 3A (approximately 3 g) was fitted to the flask. The mixture was heated for 12 hours under azeotropic reflux conditions with the removal of water. After the reaction mixture was cooled to room temperature, the solvent was evaporated under reduced pressure. The crude product thus obtained was analyzed by $^1$H NMR (DMSO-d$_6$), and the yield thereof was calculated. The results are shown in Table 4. From Table 4, it was found that a boronic acid compound E (catalyst of Example 25) having bulky 2,2,6,6-tetramethylpiperidinylmethyl groups on the 2 and 6 positions had a significantly high catalytic activity. In addition, compared with the catalytic activity of the boronic acid compound used in Example 21, the activity of a boronic acid compound (Example 27) having a 1-(2-methylimidazolyl) group on the 2 position was high in a reaction in nonan (bp: 151° C.) but was approximately equivalent in a reaction in propionitrile (bp: 97° C.)

TABLE 4

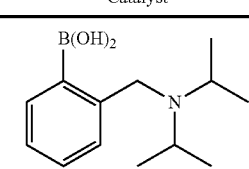

| | Catalyst | Solvent (Boiling point) | Substrate concentration | Reaction time | Yield |
|---|---|---|---|---|---|
| EXAMPLE 21 | 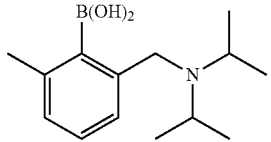 [SMILES: Cc1cccc(CN(C(C)C)C(C)C)c1B(O)O] | EtCN (97° C.) | 0.25M | 12 h | 48% |
| | | Nonane (151° C.) | 0.25M | 1.5 h | 79% |
| EXAMPLE 22 | 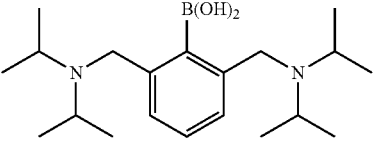 [SMILES: CC(C)N(Cc1cccc(CN(C(C)C)C(C)C)c1B(O)O)C(C)C] | EtCN (97° C.) | 0.25M | 12 h | 51% |
| EXAMPLE 23 | 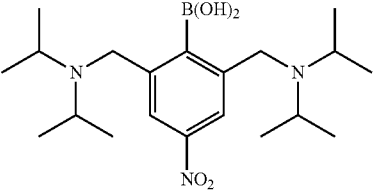 [SMILES: CC(C)N(Cc1cc([N+](=O)[O-])cc(CN(C(C)C)C(C)C)c1B(O)O)C(C)C] | EtCN (97° C.) | 0.25M | 12 h | 70% |
| EXAMPLE 24 | 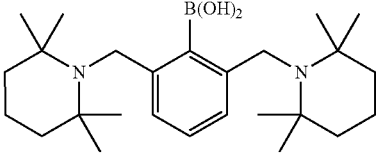 | EtCN (97° C.) | 0.25M | 12 h | 62% |
| EXAMPLE 25 |  | EtCN (97° C.) | 0.25M | 12 h | >99% |

(Boronic acid compound E)

TABLE 4-continued

| | Catalyst | Solvent (Boiling point) | Substrate concentration | Reaction time | Yield |
|---|---|---|---|---|---|
| EXAMPLE 26 | [structure: 2,6-bis((2,2,6,6-tetramethylpiperidin-1-yl)methyl)-4-nitrophenylboronic acid] | EtCN (97° C.) | 0.25M | 12 h | >99% |
| EXAMPLE 27 | [structure: 2-(1-methyl-1H-imidazol-2-yl)phenylboronic acid] | EtCN (97° C.) | 0.25M | 12 h | 42% |
| | | Nonane (151° C.) | 0.25M | 1.5 h | 91% |

Reaction scheme: phthalic acid → phthalic anhydride, Catalyst (1 mol %), Solvent, Dehydration by heating and refluxing.

Examples 28 to 32

Synthesis of a tetracarboxylic dianhydride used as a raw material for polyimide resin synthesis was investigated. In particular, in accordance with Examples 21 to 27, the dehydrative condensation reaction of a tetracarboxylic acid (2.5 mmol) shown in Table 5 was performed in butyronitrile (10 mL) in the presence of the boronic acid compound E (0.025 mmol, 1 percent by mole). After the reaction mixture was cooled to room temperature, 50 mL of pentane was added, and a precipitated solid was collected by filtration, so that a target tetracarboxylic dianhydride was obtained. In addition, in Example 32, instead of the isolated yield, the conversion yield was obtained by analysis using $^1$H NMR. The results are shown in Table 5. Each tetracarboxylic acid showed excellent reactivity, and a carboxylic dianhydride corresponding thereto was obtained in high yield (85% to 99%). Although the results obtained by reaction performed under no catalyst conditions were also shown in Table 5, the reaction hardly progressed under no catalyst conditions.

TABLE 5

Reaction scheme: Tetracarboxylic acid → Carboxylic acid dianhydrides, (Boronic acid compound E) (1 mol %), PrCN (bp 115° C., 0.25M), Dehydration by heating and refluxing, 12 h. Boronic acid compound E structure shown above.

| | Tetracarboxylic acid | Carboxylic acid dianhydrides | Isolated Yield[*1] |
|---|---|---|---|
| EXAMPLE 28 | [1,2,4,5-benzenetetracarboxylic acid] | [pyromellitic dianhydride] | 90% (7%) |
| EXAMPLE 29 | [3,3',4,4'-diphenylsulfonetetracarboxylic acid] | [3,3',4,4'-diphenylsulfonetetracarboxylic dianhydride] | 92% (0%) |

TABLE 5-continued

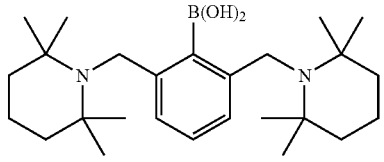

Tetracarboxyli acid —(Boronic acid compound E) (1 mol %)→ Carboxlic acid dianhydrides
PrCN (bp 115° C., 0.25M)
Dehydration by heating an refluxing, 12 h

| | Tetracarboxylic acid | Carboxylic acid dianhydrides | Isolated Yield[X1] |
|---|---|---|---|
| EXAMPLE 30 | 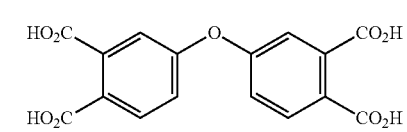 [SMILES: O=C(O)c1ccc(Oc2ccc(C(=O)O)c(C(=O)O)c2)cc1C(=O)O] | 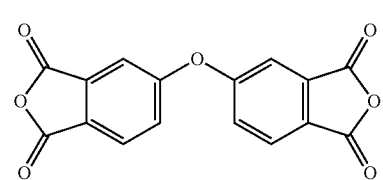 [SMILES: O=C1OC(=O)c2cc(Oc3ccc4c(c3)C(=O)OC4=O)ccc21] | 90% (3%) |
| EXAMPLE 31 | 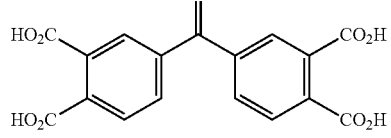 | 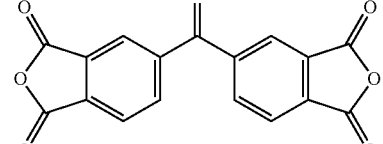 | 98% (7%) |
| EXAMPLE 32 | 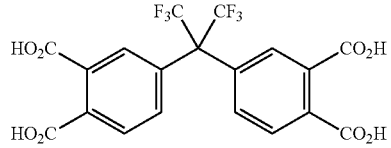 [SMILES: O=C(O)c1ccc(C(c2ccc(C(=O)O)c(C(=O)O)c2)(C(F)(F)F)C(F)(F)F)cc1C(=O)O] | 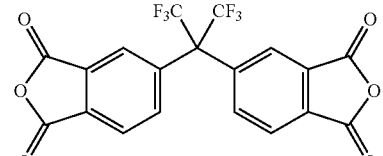 | 85%[X2] |

[X1] Value in parenthesis is yield of carboxylic acid dianhydrides when reaction was performed with no catalyst.
[X2] Conversion yield was 99% or more (based on analysis using $^1$H NMR)

Example 33

Catalytic synthesis of a diimide compound was investigated as a model reaction of polyimide synthesis. In particular, in accordance with the operation of Examples 21 to 27, a reaction between a tetracarboxylic acid (2.5 mmol) shown in Table 6 and aniline (6.3 mmol) was performed in butyronitrile (10 mL) in the presence of the boronic acid compound E (0.025 mmol, 1 percent by mole). After the reaction mixture was cooled to room temperature, a precipitated solid was collected by filtration, so that a target diimide compound was obtained (run 1 of Table 6, yield: 98%). After the filtrate was concentrated under reduced pressure, the operation was repeatedly performed 4 times (run 2 to 5) in which butyronitrile (10 mL), a tetracarboxylic acid (2.5 mmol), and aniline (5 mmol) were added to the residue, and dehydration was performed for 12 hours by heating under azeotropic reflux conditions. The results are shown in Table 6. From Table 6, the diimidization was repeatedly performed a plurality of times, and the target diimide compound was obtained in high yield (93% to 98%) without any loss of the catalytic activity. It is estimated that this diimidization reaction was probably carried out in such a way that the dehydrative condensation of two pairs of carboxylic acid groups of the tetracarboxylic acid proceeded by the aid of the boronic acid compound E as the catalyst to form the corresponding carboxylic dianhydride, and subsequently, the carboxylic dianhydride and aniline were allowed to react with each other to form the diimide compound.

In addition, the spectral data of the diimide compound thus obtained is as follows. IR(KBr) 1779, 1713, 1609, 1386, 1263, 1238, 1107 cm$^{-1}$; $^1$H NMR (400 MHz, CDCl$_3$) δ 7.39-7.59 (m, 14H), 8.02 (d, J=8.2 Hz, 2H); $^{13}$C NMR (125 MHz, DMSO-d$_6$-CDCl$_3$) δ 112.1, 123.4, 124.5, 125.6, 126.5, 127.3, 130.2, 132.9, 159.3, 164.4, 164.6; HRMS (FAB) calcd for C$_{28}$H$_{17}$N$_2$O$_5$ [M+H]$^+$ 461.1137, found 461.1159.

TABLE 6

Example 33

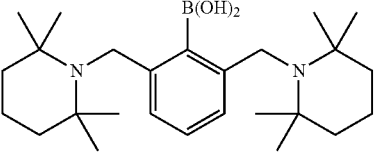

| run | 1 | 2 | 3 | 4 | 5 |
|---|---|---|---|---|---|
| Yield | 98% | 94% | 98% | 95% | 93% |

Example 34

As shown in the following formula, catalytic synthesis of a diimide compound was investigated using a tetracarboxylic acid and n-octylamine (2 equivalents). In particular, a tetracarboxylic acid (2.5 mmol), n-octylamine (5.0 mmol, 2 equivalents), an arylboronic acid catalyst (0.025 mmol, 1 percent by mole), and butyronitrile (10 mL) were added in a flask having a volume of 20 mL, and a column (small Soxhlet extractor) filled with dried molecular sieves 3A (approximately 3 g) was fitted to the flask. The mixture was heated for 12 hours under azeotropic reflux conditions with the removal of water. After the reaction mixture was cooled to room temperature, the solvent was evaporated under reduced pressure. The residue was purified by a column chromatography (silica gel, hexane-ethyl acetate 5:1→3:1→1:1), so that a diimide was obtained. The yield was 1.29 g (2.43 mmol, yield: 97%). The spectral data of the diimide thus obtained is as follows. IR (KBr) 1767, 1707, 1613, 1476, 1438, 1393, 1356, 1264, 1230, 1094, 1033 cm$^{-1}$; $^1$H NMR (CDCl$_3$, 400 MHz) δ 0.87 (t, J=6.9 Hz, 6H), 1.19-1.39 (m, 20H), 1.67 (tt, J=6.9, 7.3 Hz, 4H), 3.67 (t, J=7.3 Hz, 4H), 7.36 (dd, J=1.8, 8.2 Hz, 2H), 7.42 (d, J=1.8 Hz, 2H), 7.87 (d, J=8.2 Hz, 2H); $^{13}$C NMR (CDCl$_3$, 100 MHz) δ 14.4, 22.9, 27.1, 28.9, 29.4, 32.1, 38.6, 113.8, 124.4, 125.8, 127.9, 135.3, 161.1, 167.6, 167.8; HRMS (FAB) calcd for C$_{32}$H$_{41}$N$_2$O$_5$ [M+H]$^+$ 533.3015, found 533.3022.

Example 34

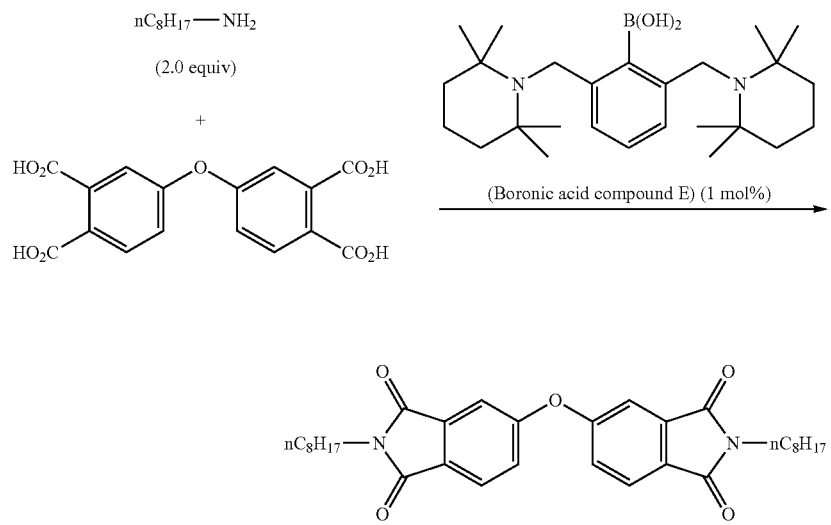

Example 35

Synthesis of an amide carboxylic acid was investigated. In particular, in accordance with Examples 21 to 27, a dehydrative condensation reaction of benzene-1,2,4,5-tetracarboxylic acid (2.5 mmol) was performed in the presence of the boronic acid compound E (0.025 mmol, 1 percent by mole). After the reaction mixture was cooled to room temperature, aniline (7.5 mmol, 3 equivalents) was added, and the mixture was stirred at room temperature for 3 hours. A precipitated solid was collected by filtration, and a target amide carboxylic acid was obtained as an isomeric mixture in a ratio of 1:1. When this amide carboxylic acid is further processed by dehydrative condensation, the corresponding diimide compound can be obtained.

The spectral data of the amide carboxylic acid thus obtained is as follows. IR (KBr) 1709, 1599, 1546, 1498, 1444, 1305, 1259, 1112 cm$^{-1}$; $^1$H NMR (400 MHz, DMSO-$d_6$) δ 7.04-7.13 (m, 2H), 7.28-7.38 (m, 4H), 7.62-7.73 (m, 4.5H), 7.95 (s, 1H), 8.31 (s, 0.5H), 10.49 (s, 1H), 10.52 (s, 1H); $^{13}$C NMR (100 MHz, DMSO-$d_6$) δ 120.6, 124.6, 128.4, 129.7, 131.6, 131.7, 133.9, 140.0, 140.1, 142.2, 142.6, 166.7, 166.8, 167.2, 167.5; HRMS (FAB) calcd for $C_{22}H_{17}N_2O_6$ [M+H]$^+$ 405.1087, found 405.1077.

Example 35 was evaporated under reduced pressure, and the yield of the corresponding carboxylic anhydride was calculated by analyzing the crude product thus obtained using $^1$H NMR (CDCl$_3$ or DMSO-$d_6$). In addition, as the solvent, propionitrile was used in Examples 36 to 39 and 41, valeronitrile was used in Example 40, and butyronitrile was used in Examples 42 and 43.

The results are shown in Table 7. In Examples 36 and 37, a cyclic-1,2-dicarboxylic acid was converted into the corresponding carboxylic anhydride in high yield. In addition, the reaction of a trans-1,2-dicarboxylic acid of Example 37 progressed concomitant with stereochemical isomerization, and as a result, a cis-carboxylic anhydride was obtained. When a reaction was performed under no catalyst conditions in Examples 36 and 37, the yield was decreased to approximately half in Example 36, and the reaction did not progress at all in Example 37. In addition, in Examples 38 and 39, a chain 1,2-dicarboxylic acid was also converted into the corresponding cyclic carboxylic anhydride in high yield. In Example 40, since the reactivity of a chain 1,3-dicarboxylic acid was relatively low, the dehydration reaction was performed by heating under azeotropic reflux conditions in valeronitrile having a high boiling point for 24 hours, so that the corresponding cyclic carboxylic anhydride was obtained in 73% yield. The reactivity of a 1,3-dicarboxylic acid used in

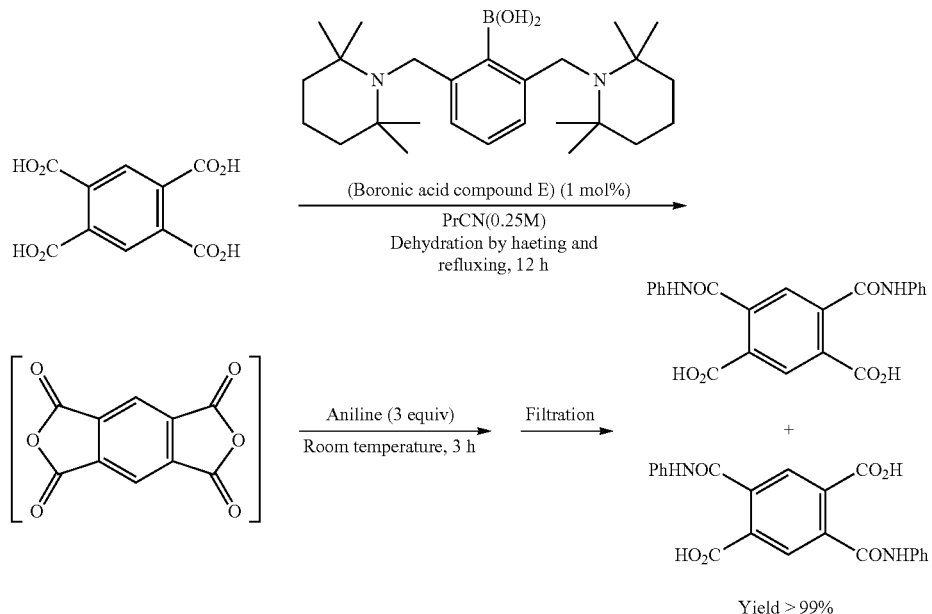

Examples 36 to 43

Synthesis of a carboxylic anhydride was performed by dehydrative condensation of an aliphatic dicarboxylic acid using the boronic acid compound E which was a highly active catalyst. In particular, in accordance with the operation of Examples 21 to 27, a dehydrative condensation reaction of an aliphatic dicarboxylic acid (2.5 mmol) shown in Table 7 was performed in a solvent (10 ml) in the presence of the boronic acid compound E (0.025 mmol, 1 percent by mole). After the reaction mixture was cooled to room temperature, the solvent Example 41 was significantly higher than that of the chain 1,3-dicarboxylic acid in Example 40, and when a dehydration reaction was performed by heating under azeotropic reflux conditions in propionitrile for 12 hours, the corresponding spiro type anhydride was obtained by conversion in 99% yield. The dehydration reaction of a chain 1,3-dicarboxylic acid in each of Examples 42 and 43 smoothly progressed in butyronitrile by heating under azeotropic reflux conditions, and the corresponding cyclic carboxylic anhydrides were obtained in respective yields of 90% and 100%.

TABLE 7

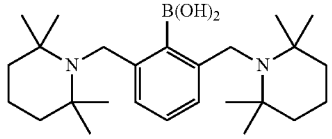

| | Aliphatic dicarboxylic acid | Carboxylic anhydride | Conversion[X1] yield |
|---|---|---|---|
| EXAMPLE 36 | 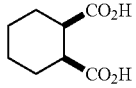 | 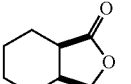 | 99% (48%) |
| EXAMPLE 37 | 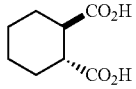 | 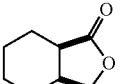 | 89% (0%) |
| EXAMPLE 38 | 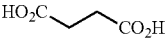 | 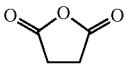 | 96% |
| EXAMPLE 39 | 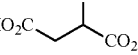 | 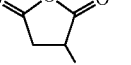 | 94% |
| EXAMPLE 40[X2] | 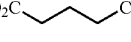 | 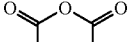 | 73% |
| EXAMPLE 41 | 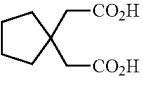 | 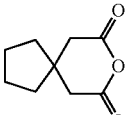 | 99% |
| EXAMPLE 42[X3] | 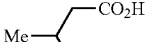 | 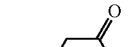 | 90% |
| EXAMPLE 43[X3] | 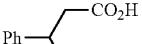 |  | 100% |

[X1]Value in parenthesis is yield of carboxylic anhydride when reactio performed with no catalyst.
[X2]Reaction was performed in valeronitrile (BuCN, bp 140° C.) for 24 hours.
[X3]Reaction was performed in butyronitrile (PrCN, bp 115° C.) for 24 hours.

The $^1$H NMR spectral data of each compound was as follows.
 Dicarboxylic acid of Example 36: δ 2.66 (m, 2H)
 Carboxylic anhydride of Example 36: δ 3.33 (m, 2H)
 Dicarboxylic acid of Example 37: δ 2.66 (m, 2H)
 Dicarboxylic acid of Example 38: δ 2.40 (s, 4H)
 Carboxylic anhydride of Example 38: δ 2.88 (s, 4H)
 Dicarboxylic acid of Example 39: δ 7.05 (d, J=8.2 Hz, 1H)
 Carboxylic anhydride of Example 39: δ 7.74 (d, J=7.8 Hz, 1H))
 Dicarboxylic acid of Example 40: δ 2.23 (t, J=7.3 Hz, 4H)
 Carboxylic anhydride of Example 40: δ 2.70 (t, J=6.0 Hz, 4H)
 Dicarboxylic acid of Example 41: δ 2.40 (s, 4H)
 Carboxylic anhydride of Example 41: δ 2.76 (s, 4H)
 Dicarboxylic acid of Example 42: δ 0.99 (d, J=6.0 Hz, 3H)
 Carboxylic anhydride of Example 42: δ 1.14 (d, J=6.3 Hz, 3H)
 Dicarboxylic acid of Example 43: δ 3.51 (m, 1H)
 Carboxylic anhydride of Example 43: δ 3.44 (m, 1H)

Example 44

The boronic acid compound E, a highly active catalyst, was synthesized as described below. That is, a 3-pentanone solution (13 ml) of 2-bromo-1,3-bis(bromomethyl)benzene (6.65 mmol), potassium carbonate (14.6 mmol), potassium iodide (1.33 mmol), and 2,2,6,6-tetramethylpiperidine (14.6 mmol) was refluxed for 48 hours. After the reaction mixture was cooled to room temperature, a precipitated solid was removed by filtration, and the filtrate was concentrated under reduced pressure. After the residue was dissolved in chloroform and was washed with water (2 times), the water layer was extracted with chloroform. The combined chloroform layer was dried over anhydrous sodium sulfate, concentrated under reduced pressure. The crude product thus obtained was purified by column chromatography (NH silica gel, eluant: hexane), so that 2-bromo-1,3-[(2,2,6,6-tetramethylpiperidine-1-yl)methyl]benzene (2.02 g, yield: 71%) was obtained. The spectral data of this compound is as follows. IR (KBr) 1458, 1381, 1366, 1262, 1175, 1132, 1017 cm$^{-1}$; $^1$H NMR (400 MHz, CDCl$_3$) δ 0.88 (br s, 12H), 1.11 (br s, 12H), 1.53 (br s, 10H), 1.74 (br s, 2H), 3.73 (s, 4H), 7.20 (t, J=7.8 Hz, 1H), 7.68 (d, J=7.8 Hz, 2H); $^{13}$C NMR (100 MHz, CDCl$_3$) δ 17.9, 21.6, 33.2, 41.3, 49.2, 54.8, 122,2, 125.2, 128.0, 142.8; HRMS (FAB) calcd for C$_{26}$H$_{44}$BrN$_2$ [M+H]$^+$ 463.2688, found 463.2704.

Next, to a THF solution (5 mL) of 2-bromo-1,3-[(2,2,6,6-tetramethylpiperidine-1-yl)methyl]benzene (1.00 mmol) was added a 1.76-M pentane solution (1.7 mL, 3.0 mmol) of tert-butyl lithium at −78° C. dropwise, and the mixture was stirred for 2.5 hours. After trimethyl borate (6.0 mmol) was added to the reaction mixture, and the mixture was stirred at room temperature performed for 3 hours. The reaction mixture was concentrated under reduced pressure, and the residue was dissolved in chloroform, washed with water (2 times). After the chloroform layer was extracted with 1-M hydrochloric acid, the pH was set to approximately 10 by adding sodium carbonate to the aqueous layer. After a precipitated solid was collected by filtration, the crude product was purified by column chromatography (NH silica gel, eluant: hexane-ethyl acetate=3:1). The obtained product was dissolved in a mixture of acetone and water, and the solvent was removed at 50° C. to 60° C. under reduced pressure, so that the boronic acid compound E (328 mg, yield: 76%) was obtained. The spectral data of this compound is as follows. IR (KBr) 3269, 1459, 1380, 1133, 1028 cm$^{-1}$; $^1$H NMR (400 MHz, CD$_3$OD-CDCl$_3$) δ 1.01 (s, 24H), 1.50-1.58 (m, 8H), 1.62 (br s, 4H), 3.66 (s, 4H) 7.23 (t, J=7.3 Hz, 1H), 7.63 (d, J=7.3 Hz, 2H); $^{13}$C NMR (100 MHz, CD$_3$OD-CDCl$_3$) δ 17.5, 41.0, 47.4, 54.4, 124.0, 127.1, 146.2; HRMS (FAB) calcd for C$_{29}$H$_{49}$BN$_2$O$_2$ [M+C$_3$H$_5$]$^+$ 469.3965, found 469.3982 (high resolution mass spectrum of this compound was measured after it was converted into an ester with 1,3-propanediol).

Example 45

The boronic acid compound used as the catalyst in Example 22 was synthesized from 2-bromo-1-(bromomethyl)-3-methylbenzene in accordance with Example 44. The spectral data of the obtained boronic acid compound is as follows. IR (KBr) 3292, 1594, 1389, 1369, 1265, 1166, 1038 cm$^{-1}$; $^1$H NMR (400 MHz, CDCl$_3$) δ 1.09 (d, J=6.9 Hz, 12H), 2.58 (s, 3H), 3.06 (sept, J=6.9 Hz, 2H), 3.75 (s, 2H), 7.04 (d, J=7.3 Hz, 1H), 7.13 (d, J=7.4 Hz, 1H), 7.17 (dd, J=7.3, 7.4 Hz, 1H); $^{13}$C NMR (125 MHz, CDCl$_3$) δ 19.9, 23.4, 47.1, 52.2, 128.6, 128.8, 129.8, 141.6, 144.7; HRMS (FAB) calcd for C$_{17}$H$_{29}$BO$_2$ [M+C$_3$H$_5$]$^+$ 290.2291, found 290.2301 (high resolution mass spectrum of this compound was measured after it was converted into an ester with 1,3-propanediol).

Example 46

The boronic acid compound used as the catalyst in Example 26 was synthesized as described below. That is, a mixture of the boronic acid compound E (0.50 mmol), nitric acid (0.82 mL, 19.5 mmol), and sulfuric acid (1.07 mL, 20 mmol) was stirred at 80° C. for 10 hours. After the reaction mixture was cooled to room temperature, by adding an aqueous solution of sodium hydroxide, the pH was set to approximately 12, and the aqueous solution was extracted with ethyl acetate (2 times). The combined organic layer was dried over sodium sulfate, and concentrated under reduced pressure. The crude product thus obtained was purified by column chromatography (NH silica gel, eluant: hexane:ethyl acetate 10:1→3:1), so that the target boronic oxide compound (94 mg, yield: 40%) was obtained. The spectral data of this compound is as follows. IR (KBr) 3512, 1515, 1461, 1347, 1261, 1173, 1132, 1063, 1027 cm$^{-1}$; $^1$H NMR (400 MHz, CD$_3$OD-CDCl$_3$) δ 1.01 (br s. 24H), 1.60 (br s, 12H), 3.73 (s, 4H), 8.46 (s, 2H); $^{13}$C NMR (100 MHz, CD$_3$OD-CDCl$_3$) δ 17.7, 41.1, 47.1, 55.0, 119.4, 148.9, 149.6; HRMS (FAB) calcd for C$_{29}$H$_{49}$BN$_3$O$_4$ [M+C$_3$H$_5$]$^+$ 514.3816, found 514.3798 (high resolution mass spectrum of this compound was measured after it was converted into an ester with 1,3-propanediol).

Example 47

The boronic acid compound used as the catalyst in Example 24 was synthesized using the boronic acid compound A instead of the boronic acid compound E of Example 46. The spectral data of the obtained boronic acid compound is as follows. IR (KBr) 1519, 1341, 1174, 1038 cm$^{-1}$; $^1$H NMR (400 MHz, CDCl$_3$) δ 1.11 (d, J=6.9 Hz, 24H), 3.03 (sept, J=6.9 Hz, 4H), 3.90 (s, 4H), 8.06 (s, 2H); $^{13}$C NMR (125 MHz, CDCl$_3$) δ 20.0, 47.4, 52.1, 125.2, 145.1, 147.5; HRMS (FAB) calcd for C$_{23}$H$_{41}$BN$_3$O$_4$ [M+C$_3$H$_5$]$^+$ 434.3190, found 434.3216 (high resolution mass spectrum of this compound was measured after it was converted into an ester with 1,3-propanediol).

This application claims the benefit of Japanese Patent Application No. 2009-058720 filed Mar. 11, 2009, which is hereby incorporated by reference herein in its entirety.

Industrial Applicability

The present invention can be applied mainly to pharmaceutical and chemical industries and can be used when various carboxylic anhydrides are produced which are used, for example, as raw materials of thermoplastic aromatic polyimides besides intermediates of drugs, agricultural chemicals, cosmetics, and the like.

The invention claimed is:

1. An arylboronic acid compound having —CH$_2$NR$^1$R$^2$ on each of the two ortho positions, wherein R$^1$ and R$^2$ each independently represent a branched alkyl group, an alkyl group having a cycloalkyl group, an alkyl group having a halogen atom, a cycloalkyl group, a cycloalkyl group having an alkyl group, or a cycloalkyl group having a halogen atom, or R$^1$ and R$^2$ are bonded to each other to form a nitrogen-containing 6-membered hetero ring in the form of NR$^1$R$^2$.

2. The arylboronic acid compound according to claim 1, wherein the —CH$_2$NR$^1$R$^2$ represents a diisopropylaminomethyl group or a trioctylammonium methyl group.

3. The arylboronic acid compound according to claim 1, wherein the —CH$_2$NR$^1$R$^2$ is a group represented by the following formula (1)

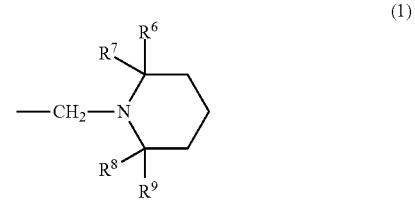

(1)

wherein R$^6$ to R$^9$ each independently represent an alkyl group or an alky group having a halogen atom.

4. The arylboronic acid compound according to claim 1, further comprising on its benzene ring a halogen atom, an alkyl group, a nitro group, or an alkyl group having a halogen atom.

* * * * *